United States Patent

Hofer et al.

[11] 3,973,013
[45] Aug. 3, 1976

[54] SUBSTITUTED S-CARBOXYMETHYL-(THIONO)-(DI)-THIOL-PHOSPHONIC ACID ESTERS AND ESTER-AMIDES AND INSECTICIDAL COMPOSITION AND METHOD

[75] Inventors: Wolfgang Hofer; Fritz Maurer; Hans-Jochem Riebel; Lothar Rohe, all of Wuppertal; Wolfgang Behrenz, Overath-Steinenbrueck; Ingeborg Hammann, Cologne; Wilhelm Stendel, Wuppertal, all of Germany

[73] Assignee: Bayer Aktiengesellschaft, Leverkusen, Germany

[22] Filed: Mar. 10, 1975

[21] Appl. No.: 556,984

[30] Foreign Application Priority Data

Mar. 15, 1974  Germany............................ 2412429

[52] U.S. Cl. ............................... 424/212; 260/940; 260/941; 260/942; 424/210
[51] Int. Cl.² ....................... A01N 9/36; C07F 9/40
[58] Field of Search ........... 260/940, 941, 942, 950, 260/951; 424/210, 212

[56] References Cited
UNITED STATES PATENTS

| | | | |
|---|---|---|---|
| 3,306,898 | 2/1967 | Sehring et al. | 260/941 X |
| 3,562,362 | 2/1971 | Kezerian | 260/942 |
| 3,689,605 | 9/1972 | Santi | 260/941 X |
| 3,692,902 | 9/1972 | Tatsumi et al. | 260/941 X |

FOREIGN PATENTS OR APPLICATIONS

| | | | |
|---|---|---|---|
| 1,188,859 | 3/1965 | Germany | 260/941 |
| 1,191,991 | 4/1965 | Germany | 260/941 |

*Primary Examiner*—Richard L. Raymond
*Attorney, Agent, or Firm*—Burgess, Dinklage & Sprung

[57] ABSTRACT

Substituted S-carboxymethyl-(thiono)-(di)-thiolphosphoric(phosphonic) acid esters and ester-amides of the formula

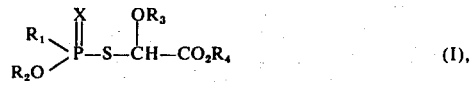

in which
$R_1$ is phenyl, $C_1$–$C_6$ alkoxy, $C_1$–$C_6$ alkylmercapto, $C_1$–$C_5$ alkyl, alkoxyalkoxy with 1 to 5 carbon atoms in each alkyl moiety, $C_1$–$C_5$ alkylamino or $C_2$–$C_5$ alkenylamino, $R_2$ is $C_1$–$C_6$ alkyl, alkoxyalkyl with 1 to 5 carbon atoms in each alkyl moiety or $C_5$–$C_7$ cycloalkyl, $R_3$ is phenyl; cyclohexyl; $C_1$–$C_7$ alkyl; $C_1$–$C_5$ halogenoalkyl; or carbalkoxymethyl, aralkyl or alkoxyalkyl with 1 to 5 carbon atoms in each alkyl moiety, $R_4$ is $C_1$–$C_5$ alkyl, phenyl or phenyl substituted by at least one of halogen, nitrile, nitro, $C_1$–$C_4$ alkyl and $C_1$–$C_4$ alkoxy, and X is oxygen or sulfur, which possess insecticidal properties.

10 Claims, No Drawings

SUBSTITUTED S-CARBOXYMETHYL-(THIONO)-(DI)-THIOL-PHOSPHONIC ACID ESTERS AND ESTER-AMIDES AND INSECTICIDAL COMPOSITION AND METHOD

The present invention relates to and has for its objects the provision of particular new substituted S-carboxymethyl-(thiono)-(di)-thiolphosphoric(phosphonic) acid esters and ester-amides which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known from U.S. Pat. No. 3,007,845 and German Published Specification DAS No. 1,068,699 that certain substituted S-carboxy-methyl-(thiono)thiolphosphoric acid esters, for example O,O-dimethyl-(Compound A) and O,O-diethyl-S-(1-ethylmercapto-1-carbethoxymethyl)-thionothiolphosphoric acid ester (Compound B), and S-carbamoylmethylthionothiolphosphoric acid esters, for example O,O-dimethyl-S-(1-methyl-1-N-methylcarbamoylmethyl)-thionothiolphosphoric acid ester (Compound C), possess insecticidal properties.

The present invention provides, as new compounds, the substituted S-carboxymethyl(thiono)-(di)-thiolphosphoric (phosphonic) acid esters and ester-amides of the general formula

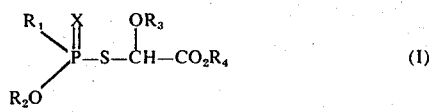

in which
R$_1$ is phenyl, C$_1$–C$_6$ alkoxy, C$_1$–C$_6$ alkylmercapto, C$_1$–C$_5$ alkyl, alkoxyalkoxy with 1 to 5 carbon atoms in each alkyl moiety, C$_1$–C$_5$ alkylamino or C$_2$–C$_5$ alkenylamino,
R$_2$ is C$_1$–C$_6$ alkyl, alkoxyalkyl with 1 to 5 carbon atoms in each alkyl moiety or C$_5$–C$_7$ cycloalkyl,
R$_3$ is phenyl; cyclohexyl; C$_1$–C$_7$ alkyl; C$_1$–C$_5$ halogenoalkyl, or carbalkoxymethyl, aralkyl or alkoxyalkyl with 1 to 5 carbon atoms in each alkyl moiety,
R$_4$ is C$_1$–C$_5$ alkyl, phenyl or phenyl substituted by at least one of halogen, nitrile, nitro, C$_1$–C$_4$ alkyl and C$_1$–C$_4$ alkoxy, and
X is oxygen or sulfur.

Preferably R$_1$ represents straight-chain or branched C$_1$–C$_4$ alkyl, C$_1$–C$_4$ alkoxy, C$_1$–C$_4$ alkylmercapto, C$_1$–C$_4$ monoalkylamino, alkoxyalkoxy with 1 to 4 carbon atoms per alkyl moiety, C$_2$–C$_4$ monoalkenylamino or phenyl, R$_2$ is straight-chain or branched C$_1$–C$_4$ alkyl, C$_5$–C$_6$ cycloalkyl or alkoxyalkyl with 1 to 4 (especially 1 to 3) carbon atoms per alkyl moiety, R$_3$ is straight-chain or branched C$_1$–C$_6$ alkyl, halogenoalkyl with 1 to 4 (especially 1 to 3) carbon atoms, carbalkoxymethyl with 1 to 4 carbon atoms in the alkyl moiety, alkoxyalkyl with 1 to 4 (especially 1 to 3) carbon atoms per alkyl moiety, aralkyl with 1 to 4 (especially 1 to 3) carbon atoms in the alkyl moiety, phenyl or cyclohexyl, and R$_4$ is straight-chain or branched C$_1$–C$_4$ alkyl, phenyl or phenyl substituted by at least one of nitro, chlorine, bromine, methyl, ethyl, methoxy and ethoxy.

Surprisingly, the substituted S-carboxymethyl(thiono)-(di)-thiolphosphoric(phosphonic) acid esters and ester-amides according to the invention show a better insecticidal action than previously known compounds of analogous structure and of the same type of action. The new compounds can be employed against insects which damage plants, pests harmful to health, pests of stored products and, in the veterinary medicine field, against animal ectoparasites, for example parasitic fly larvae.

The invention also provides a process for the preparation of a substituted S-carboxymethyl-(thiono)-(di)-thiol-phosphoric(phosphonic) acid ester or ester-amide of (thiono)-(di)-thiol-phosphoric(phosphonic) formula (I) in which a salt of a (thiono)-(di)-thiolphosphoric(phoshonic) acid ester or ester-amide of the general formula

in which
R$_1$, R$_2$ and X have the above-mentioned meanings, and
M is an alkali metal, alkaline earth metal or ammonium equivalent,
is reacted with a substituted halogenoacetic acid ester of the general formula

in which
R$_3$ and R$_4$ have the above-mentioned meanings, and Hal is halogen, preferably chlorine or bromine.

If, for example, bromo-isopropoxy-acetic acid 4-cyanophenyl ester and the potassium salt of O,O-dimethylthionothiolphosphoric acid ester are used as starting materials, the course of the reaction can be represented by the following equation:

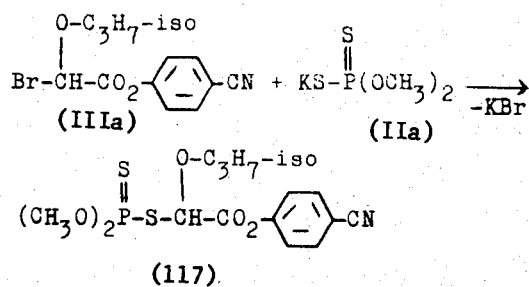

The salts of the(thiono)-(di)-thiolphosphoric(phosphonic) acid esters and ester-amides (II) to be used as starting materials are in most cases known and they can be prepared according to customary processes, for example by treating the corresponding ester halides or ester-amide halides with hydrogen sulfide in the presence of carbonates, or with alcoholic alkali:

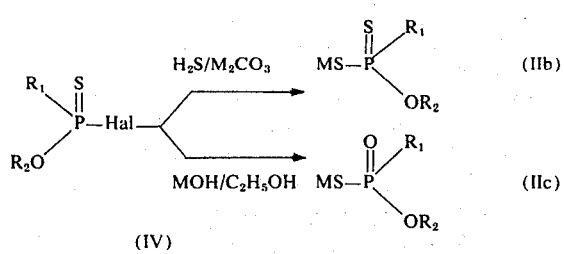

The following may be mentioned as examples thereof: the sodium salts and potassium salts of O,O-dimethyl-, O,O-diethyl-, O,O-di-n-propyl-, O,O-di-isopropyl-, O,O-di-n-butyl-, O,O-di-sec.-butyl-, O,O-di-tert.-butyl-, O,O-di-isobutyl-, O-ethyl-O-n-propyl-, O-ethyl-O-isopropyl-, O-ethyl-O-tert.-butyl-, O-methyl-O-cyclohexyl-, O-ethyl-O-cyclohexyl-, O-n-propyl-O-cyclohexyl-, O-isopropyl-O-cyclohexyl-, O-n-butyl-O-cyclohexyl-, O-tert.-butyl-O-cyclohexyl-, O-sec.-butyl-O-cyclohexyl-, O-methyl-O-(methoxymethyl)-, O-ethyl-O-(methoxymethyl)-, O-n-propyl-O-(methoxymethyl)-, O-ethyl-O-(ethoxyethyl)-, O-n-propyl-O-(ethoxyethyl)-, O-isopropyl-O-(ethoxyethyl)-, O-ethyl-O-(n-propoxyethyl)-O-n-propyl-O-(n-propoxyethyl)- and O-ethyl-O-(isopropoxyethyl)-thiolphosphoric acid diesters and the corresponding thiono analogues; O,S-dimethyl-, O,S-diethyl-, O,S-di-n-propyl-, O,S-di-isopropyl-, O,S-di-n-butyl-, O,S-di-isobutyl-, O,S-di-tert.-butyl-, O-ethyl-S-methyl-, O-ethyl-S-n-propyl-, O-ethyl-S-tert.-butyl-, O-n-propyl-S-ethyl-, O-isopropyl-S-ethyl, O-n-butyl-S-ethyl-, O-ethoxymethyl-S-ethyl-, O-ethoxyethyl-S-ethyl-, O-n-propoxyethyl-S-n-propyl- and O-isopropoxyethyl-S-n-propyl-dithiolphosphoric acid diester and their thiono analogues; O-methyl-N-methyl-, O-methyl-N-ethyl-, O-methyl-N-n-propyl-, O-methyl-N-isopropyl-, O-methyl-N-n-butyl-, O-methyl-N-sec.-butyl-, O-ethyl-N-methyl-, O-ethyl-N-n-propyl, O-ethyl-N-isopropyl-, O-ethyl-N-tert.-butyl-, O-n-propyl-N-ethyl, O-n-propyl-N-isopropyl-, O-n-butyl-N-ethyl-, O-tert.-butyl-N-ethyl-, O-sec.-butyl-N-ethyl-, O-methyl-N-allyl-, O-ethyl-N-allyl-, O-n-propyl-N-allyl-, O-isopropyl-N-allyl-, O-n-butyl-N-allyl-, O-tert.-butyl-N-allyl-, O-ethyl-N-butenyl(2)-, O-n-propyl-N-butenyl(2)-, O-tert.-butyl-N-butenyl(2)-, O-ethoxyethyl-N-allyl-, O-ethoxyethyl-N-ethyl-, O-ethoxyethyl-N-n-propyl-, O-ethoxyethyl-N-n-butyl-, O-n-propoxyethyl-N-ethyl-, O-n-propoxyethyl-N-butenyl(2)-, O-cyclohexyl-N-ethyl-, O-cyclohexyl-N-allyl- and O-cyclohexyl-N-propenyl-thiolphosphoric acid ester amides and their thiono analogues; O-methyl-, O-ethyl-, O-n-propyl-, O-isopropyl-, O-n-butyl-, O-sec.-butyl-, O-tert.-butyl-, O-cyclohexyl-, O-methoxymethyl-, O-ethoxyethyl-, O-n-propoxyethyl, O-n-butoxyethyl-methane-, ethane-, n-propane, n-butane-, sec.-butane-, isopropane- and benzene-thiolphosphonic acid esters and their thiono analogues; and S-methyl-, S-ethyl-, S-n-propyl-, S-isopropyl-, S-n-butyl-, S-sec.-butyl-, S-tert.-butyl-methane-, ethane-, n-propane-, isopropane-, n-butane-, sec-butane-, tert.-butane- and benzene-dithiolphosphonic acid ester and their thiono analogues.

The substituted halogenoacetic acid esters (III), some of which are new, can be prepared according to processes which are known in principle, for example by reaction of the corresponding substituted acetic acid esters with halogen under UV irradiation, or by reaction with N-bromosuccinimide.

The following may be mentioned as examples of halogenoacetic acid esters (III) to be reacted in accordance with the process: methoxy-, ethoxy-, n-propoxy-, isopropoxy-, n-butoxy-, isobutoxy-, tert.-butoxy-, n-pentoxy-, n-hexoxy-, chloromethoxy-, 2-chloroethoxy-, 3-chloropropoxy-, ethoxymethoxy-, ethoxyethoxy-, ethoxypropoxy-, n-propoxyethoxy-, phenoxy-, cyclohexoxy-, carbethoxymethoxy-, carbomethoxymethoxy-, carbo-n-propoxy-methoxy-, carbo-n-butoxymethoxy-, 2-phenylethoxy- and benzyloxy-bromo- or chloroacetic acid ethyl, methyl, n-propyl, isopropyl, n-butyl, iso-butyl, tert.-butyl, phenyl, 4-nitrophenyl, 2-nitrophenyl, 2-chlorophenyl, 2-bromo-phenyl, 4-chlorophenyl, 4-bromophenyl, 2,4-dichlorophenyl, 2,4-dibromophenyl, 3-methoxyphenyl, 3-ethoxyphenyl, 2-methyl-4-chlorophenyl, 2-ethyl-4-chlorophenyl, 2-methoxyphenyl, 2,5dichlorophenyl, 2,5-dimethylphenyl or 2,5-diethylphenyl esters.

The preparative process is preferably carried out in the presence of suitable solvents and diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperaure can be varied within a fairly wide range. In general, the reaction is carried out at between 5° and 100°C, preferably at from 10° to 30°C.

To carry out the process, the starting materials are in general employed in equimolar amounts. An excess of one or other reactant in general produces no significant advantages. The reaction is preferably carried out in the presence of one of the above-mentioned solvents, at the temperatures indicated. After a reaction time of one or more hours, in most cases at an elevated temperature, the batch is cooled and the reaction mixture is poured into water and taken up in an organic solvent, for example benzene. The reaction mixture is then worked up in the usual manner by drying the organic phase, evaporating the solvent and, if appropriate, distilling the residue.

The new compounds are obtained in the form of oils which in some cases cannot be distilled without decomposition but can be freed from the last volatile constituents by so-called "slight distillation", that is to say prolonged heating under reduced pressure to moderately elevated temperatures, and can be purified in this way. They are characterized by their refractive indexes.

As has already been mentiond, the substituted S-carboxymethyl-(thiono)-(di)-thiolphosphoric(phosphonic) acid esters and ester-amides according to the invention are distinguished by an outstanding insecticidal activity. They are active against plant pests, pests harmful to health, pest of stored products and, in the veterinary medicine field, against animal parasites (ectoparasites), for example parasitic fly larvae, and combine a low phytotoxicity with a good action against both sucking and biting insects.

For this reason, the compounds according to the invention can be employed successfully as pesticides in plant protection and in the hygiene field, the field of stored products and the veterinary field.

To the sucking insects there belong, in the main aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra or Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea or Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little capitatafly (*Fannia canicularis*), the block blow fly (*Phormia regina*) and bluebottle fly (*Caliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocabons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides or nematocides, acaricides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

The substituted halogenoacetic acid esters (III) used as starting materials are prepared, for example, in the following manner:

Method A

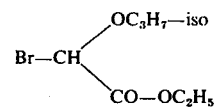

A solution of 0.5 g of dibenzoyl peroxide in 95 g (0.65 mole) of isopropoxyacetic acid ethyl ester was added dropwise to a suspension of 115.7 g (0.65 mole) of N-bromosuccinimide in 800 ml of carbon tetrachloride at 80°C. After the exothermic reaction had subsided, the batch was additionally boiled under reflux for ½ hour. The succinimide was then filtered off and the solvent was removed by distillation under reduced pressure. The residue was distilled. This gave 90 g (61% of theory) of bromo-isopropoxyacetic acid ethyl ester of boiling point 99°–102°C/15 mm Hg.

Method B

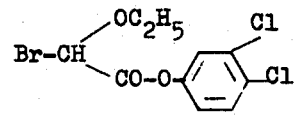

16 g (0.1 mole) of bromine were added dropwise to 24.9 g (0.1 mole) of ethoxyacetic acid 3,4-dichlorophenyl ester at 130° to 140°C, while irradiating with UV light. The reaction mixture was then additionally stirred for 10 minutes at 130°C. After cooling, the batch was dissolved in 300 ml of methylene chloride and the solution was washed with saturated sodium bicarbonate solution and dried over sodium sulfate. The solvent was stripped off under reduced pressure. This gave 28.2 g (86% of theory) of bromoethoxyacetic acid 3,4-dichlorophenyl ester in the form of a brown oil having a refractive index $n_D^{24}$ of 1.6183.

The following compounds were prepared analogously:

Table 1

$$Br-CH\begin{matrix}OR_3\\CO-OR_4\end{matrix} \quad (IIIb)$$

| $R_3$ | $R_4$ | Process | Yield (% of theory) | Physical properties |
|---|---|---|---|---|
| $C_2H_5$ | $C_2H_5$ | A | 93 | $n_D^{26}$: 1.4586 |

Table 1-continued $$Br-CH\underset{CO-OR_4}{\overset{OR_3}{\diagup}} \quad (IIIb)$$

| $R_3$ | $R_4$ | Process | Yield (% of theory) | Physical properties |
|---|---|---|---|---|
| $C_2H_5$ | $C_3H_7$-iso | A | 60 | b.p. 52–54°C/0.1 mmHg |
| ⟨phenyl⟩ | $C_2H_5$ | A | 63 | b.p. 85–88°C/0.1 mmHg |
| $CH_3$ | n-$C_4H_9$ | A | 46 | b.p. 121–125°C/22 mm Hg |
| ⟨cyclohexyl⟩ | $C_2H_5$ | A | 76 | b.p. 100–104°C/0.01 mm Hg |
| $C_2H_5$ | $CH_3$ | A | 71 | b.p. 86–90°C/15 mm Hg |
| $CH_2$—CO—$OC_2H_5$ | $C_2H_5$ | A | 97 | $n_D^{23}$: 1.4630 |
| n-$C_3H_7$ | $C_2H_5$ | A | 93 | $n_D^{23}$: 1.4570 |
| $C_3H_7$—iso | $C_3H_7$—iso | A | 94 | $n_D^{24}$: 1.4504 |
| n-$C_6H_{13}$ | $C_2H_5$ | A | 98 | $n_D^{23}$: 1.4600 |
| $CH_2$—$CH_2$—$OCH_3$ | $C_2H_5$ | A | 87 | $n_D^{25}$: 1.4613 |
| $CH_2-CH_2$—⟨phenyl⟩ | $C_2H_5$ | A | 96 | $n_D^{22}$: 1.5263 |
| $C_2H_5$ | $CH\underset{C_2H_5}{\overset{CH_3}{\diagup}}$ | A | 99 | $n_D^{24}$: 1.4678 |
| $CH\underset{C_2H_5}{\overset{CH_3}{\diagup}}$ | $C_2H_5$ | A | 83 | $n_D^{24}$: 1.4779 |
| $CH\underset{C_2H_5}{\overset{CH_3}{\diagup}}$ | $C_3H_7$—iso | A | 89 | $n_D^{22}$: 1.4532 |
| $C_2H_5$ | ⟨phenyl⟩-Cl | B | 80 | $n_D^{24}$: 1.6031 |
| $C_2H_5$ | -⟨phenyl⟩-Br | B | 86 | $n_D^{24}$: 1.6145 |
| $C_2H_5$ | -⟨phenyl⟩-$NO_2$ | B | 77 | $n_D^{24}$: 1.5987 |
| $C_2H_5$ | -⟨phenyl⟩-Cl / $CH_3$ | B | 82 | $n_D^{24}$: 1.6012 |
| $C_2H_5$ | -⟨phenyl⟩ | B | 77 | $n_D^{24}$: 1.5887 |
| $C_2H_5$ | ⟨phenyl⟩-$OCH_3$ | B | 73 | $n_D^{24}$: 1.5911 |
| $C_2H_5$ | -⟨phenyl⟩-Cl, Cl | B | 78 | m.p. 52°C |
| $CH_2$—$CH_2$—Cl | $C_2H_5$ | A | 74 | $n_D^{22}$: 1.4788 |

EXAMPLE 2

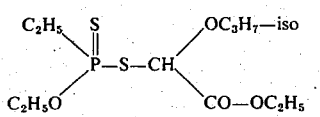

$$\underset{C_2H_5O}{\overset{C_2H_5}{\diagdown}}\overset{S}{\underset{\|}{P}}-S-CH\underset{CO-OC_2H_5}{\overset{OC_3H_7-iso}{\diagup}} \quad (1)$$

17 g (0.08 mole) of the potassium salt of ethanedithiophosphonic acid O-ethyl ester, dissolved in about 200 ml of acetonitrile, were added to a solution of 18 g (0.08 mole) of bromo-isopropoxyacetic acid ethyl ester in 80 ml of acetonitrile and the reaction mixture was stirred for a further hour at 20° to 30°C and was then poured into a mixture of 500 ml of water and 500 ml of toluene. After thorough shaking, the aqueous phase was separated off; the organic solution was additionally extracted by shaking twice with 300 ml of water at a time and was then dried over sodium sulfate. After distilling off the solvent, the residue was subjected to "slight distillation" under greatly reduced pressure at 40° to 50°C.

This gave 21 g (84% of theory) of O-ethyl-S-(1-isopropoxy -1-carbethoxy-methyl)-ethanethionothiolphosphonic acid ester in the form of a yellow oil having a refractive index $n_D^{22}$ of 1.5002.

The following compounds of the general formula (I) were prepared analogously:

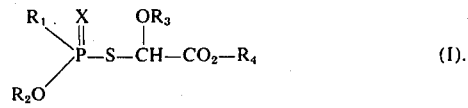

(I).

Table 2

| Compound No. | R₁ | R₂ | R₃ | R₄ | X | Yield (% of theory) | Refractive index |
|---|---|---|---|---|---|---|---|
| 2 | $C_2H_5$ | $C_2H_5$ | $C_2H_5$ | $C_2H_5$ | S | 73 | $n_D^{24}$: 1.5022 |
| 3 | $NH-C_3H_7-iso$ | $C_2H_5$ | $C_2H_5$ | $C_2H_5$ | S | 85 | $n_D^{24}$: 1.5042 |
| 4 | $OC_2H_5$ | $C_2H_5$ | $C_2H_5$ | $C_2H_5$ | S | 79 | $n_D^{24}$: 1.4892 |
| 5 | $C_2H_5$ | $C_2H_5$ | $C_2H_5$ | Cl-C₆H₃-Cl (2,?-dichlorophenyl) | S | 45 | $n_D^{21}$: 1.5532 |
| 6 | $C_2H_5$ | $C_2H_5$ | $C_2H_5$ | $C_3H_7-iso$ | S | 70 | $n_D^{23}$: 1.4968 |
| 7 | phenyl | $C_2H_5$ | $C_2H_5$ | $C_3H_7-iso$ | O | 84 | $n_D^{23}$: 1.5129 |
| 8 | $C_2H_5$ | $C_2H_5$ | phenyl | $C_2H_5$ | S | 76 | $n_D^{21}$: 1.5428 |
| 9 | $C_2H_5$ | $C_2H_5$ | $CH_3$ | $n-C_4H_9$ | S | 73 | $n_D^{21}$: 1.5042 |
| 10 | phenyl | $C_2H_5$ | $CH_3$ | $n-C_4H_9$ | O | 65 | $n_D^{22}$: 1.5170 |
| 11 | $OC_2H_5$ | $C_2H_5$ | $C_3H_7-iso$ | $C_2H_5$ | S | 83 | $n_D^{22}$: 1.4878 |
| 12 | $C_2H_5$ | $C_2H_5$ | cyclohexyl | $C_2H_5$ | S | 68 | $n_D^{21}$: 1.5114 |
| 13 | $OC_2H_5$ | $C_2H_5$ | cyclohexyl | $C_2H_5$ | S | 79 | $n_D^{21}$: 1.5007 |
| 14 | phenyl | $C_2H_5$ | $C_3H_7-iso$ | $C_2H_5$ | O | 65 | $n_D^{21}$: 1.5152 |
| 15 | $C_2H_5$ | $C_2H_5$ | $C_2H_5$ | $CH_3$ | S | 80 | $n_D^{17}$: 1.5160 |
| 16 | $OC_2H_5$ | $C_2H_5$ | $C_2H_5$ | $CH_3$ | S | 73 | $n_D^{16}$: 1.4998 |
| 17 | phenyl | $C_2H_5$ | $C_2H_5$ | $CH_3$ | O | 85 | $n_D^{20}$: 1.5278 |
| 18 | phenyl | $C_2H_5$ | $C_2H_5$ | $C_2H_5$ | O | 83 | $n_D^{17}$: 1.5187 |
| 19 | $O-CH_2-CH_2-OC_2H_5$ | $C_2H_5$ | $C_2H_5$ | $C_2H_5$ | S | 85 | $n_D^{16}$: 1.4897 |
| 20 | $O-CH_2-CH_2-OC_2H_5$ | $C_2H_5$ | $C_2H_5$ | $CH_3$ | S | 67 | $n_D^{16}$: 1.4958 |
| 21 | $C_2H_5$ | $CH_2-CH_2-OC_2H_5$ | $C_2H_5$ | $C_2H_5$ | S | 89 | $n_D^{23}$: 1.5002 |
| 22 | $C_2H_5$ | $CH_2-CH_2-OC_2H_5$ | $C_3H_7-iso$ | $C_2H_5$ | S | 86 | $n_D^{23}$: 1.4958 |
| 23 | $C_2H_5$ | $CH_2-CH_2-OC_2H_5$ | $C_2H_5$ | $CH_3$ | S | 69 | $n_D^{22}$: 1.5073 |
| 24 | $O-CH_2-CH_2-OC_2H_5$ | $C_2H_5$ | $C_2H_5$ | Cl-C₆H₃-Cl | S | 49 | $n_D^{21}$: 1.5403 |
| 25 | $OC_2H_5$ | $C_2H_5$ | phenyl | $C_2H_5$ | S | 67 | $n_D^{20}$: 1.5324 |
| 26 | $O-CH_2-CH_2-OC_2H_5$ | $C_2H_5$ | phenyl | $C_2H_5$ | S | 73 | $n_D^{21}$: 1.5265 |
| 27 | $OCH_3$ | $CH_3$ | $C_2H_5$ | $C_2H_5$ | S | 34 | $n_D^{21}$: 1.4998 |
| 28 | $C_2H_5$ | $C_2H_5$ | $CH_2-CO-OC_2H_5$ | $C_2H_5$ | S | 65 | $n_D^{22}$: 1.5033 |
| 29 | $OC_2H_5$ | $C_2H_5$ | $CH_2-CO-OC_2H_5$ | $C_2H_5$ | S | 78 | $n_D^{22}$: 1.4900 |
| 30 | $OCH_3$ | $CH_3$ | $CH_2-CO-OC_2H_5$ | $C_2H_5$ | S | 65 | $n_D^{22}$: 1.4930 |
| 31 | $CH_3$ | $C_2H_5$ | $C_3H_7-iso$ | $C_2H_5$ | S | 63 | $n_D^{22}$: 1.5013 |
| 32 | $CH_3$ | $C_2H_5$ | $C_2H_5$ | $C_2H_5$ | S | 63 | $n_D^{20}$: 1.1924 |
| 33 | $OCH_3$ | $CH_3$ | $C_3H_7-iso$ | $C_2H_5$ | S | 57 | $n_D^{22}$: 1.4913 |
| 34 | $C_2H_5$ | $CH_3$ | $n-C_3H_7$ | $C_2H_5$ | S | 84 | $n_D^{26}$: 1.5011 |
| 35 | $OCH_3$ | $CH_3$ | $n-C_3H_7$ | $C_2H_5$ | S | 76 | $n_D^{26}$: 1.4946 |
| 36 | $C_2H_5$ | $CH_3$ | $n-C_3H_7$ | $C_2H_5$ | S | 83 | $n_D^{26}$: 1.5067 |
| 37 | $C_2H_5$ | $CH_3$ | $C_2H_5$ | $C_2H_5$ | S | 87 | $n_D^{22}$: 1.5076 |
| 38 | $C_2H_5$ | $CH_3$ | $C_3H_7-iso$ | $C_2H_5$ | S | 76 | $n_D^{22}$: 1.5036 |

Table 2-continued

| Compound No. | R₁ | R₂ | R₃ | R₄ | X | Yield (% of theory) | Refractive index |
|---|---|---|---|---|---|---|---|
| 39 | $C_2H_5$ | $CH_3$ | $CH_2-CO-OC_2H_5$ | $C_2H_5$ | S | 79 | $n_D^{23}$: 1.5060 |
| 40 | $C_2H_5$ | $C_2H_5$ | $C_3H_7$—iso | $C_3H_7$—iso | S | 85 | $n_D^{25}$: 1.4940 |
| 41 | $OCH_3$ | $CH_3$ | $C_3H_7$—iso | $C_3H_7$—iso | S | 57 | $n_D^{25}$: 1.4840 |
| 42 | $CH_3$ | $C_2H_5$ | $C_3H_7$—iso | $C_3H_7$—iso | S | 58 | $n_D^{25}$: 1.4920 |
| 43 | $C_2H_5$ | $CH_3$ | $C_3H_7$—iso | $C_3H_7$—iso | S | 80 | $n_D^{25}$: 1.4975 |
| 44 | $C_2H_5$ | $C_3H_7$—n | $C_2H_5$ | $C_2H_5$ | S | 76 | $n_D^{24}$: 1.5000 |
| 45 | $C_2H_5$ | $C_3H_7$—n | $C_3H_7$—iso | $C_2H_5$ | S | 66 | $n_D^{24}$: 1.4966 |
| 46 | $C_2H_5$ | $C_3H_7$—n | $C_3H_7$—iso | $C_3H_7$—iso | S | 82 | $n_D^{24}$: 1.4912 |
| 47 | $C_2H_5$ |  | $C_2H_5$ | $C_2H_5$ | S | 75 | $n_D^{25}$: 1.5143 |
| 48 | $C_2H_5$ | $C_2H_5$ | $n-C_6H_{13}$ | $C_2H_5$ | S | 82 | $n_D^{23}$: 1.4958 |
| 49 | $OCH_3$ | $CH_3$ | $n-C_6H_{13}$ | $C_2H_5$ | S | 66 | $n_D^{23}$: 1.4860 |
| 50 | $C_2H_5$ | $CH_3$ | $n-C_6H_{13}$ | $C_2H_5$ | S | 84 | $n_D^{21}$: 1.5003 |
| 51 | $C_2H_5$ | $C_2H_5$ | $CH_2-CH_2-OCH_3$ | $C_2H_5$ | S | 67 | $n_D^{23}$: 1.5048 |
| 52 | $C_2H_5$ | $C_3H_7$—n | $C_2H_5$ | $CH_3$ | S | 73 | $n_D^{25}$: 1.5205 |
| 53 | $C_2H_5$ | $C_3H_7$—n | $n-C_6H_{13}$ | $C_2H_5$ | S | 81 | $n_D^{25}$: 1.4913 |
| 54 | $C_2H_5$ | $CH_3$ | $C_2H_5$ | $CH_3$ | S | 70 | $n_D^{23}$: 1.535 |
| 55 | $OCH_3$ | $CH_3$ | $C_2H_5$ | $CH_3$ | S | 70 | $n_D^{23}$: 1.5100 |
| 56 | $OCH_3$ | $CH_3$ | $CH_2-CH_2-OCH_3$ | $C_2H_5$ | S | 55 | $n_D^{23}$: 1.4965 |
| 57 | $OC_2H_5$ | $C_2H_5$ | $C_3H_7$—iso | $C_2H_5$ | O | 87 | $n_D^{23}$: 1.4570 |
| 58 | $C_2H_5$ | $C_2H_5$ | $CH_2-CH_2Cl$ | $C_2H_5$ | S | 68 | $n_D^{22}$: 1.5123 |
| 59 | $C_2H_5$ | $CH_3$ | $CH_2-CH_2OCH_3$ | $C_2H_5$ | S | 70 | $n_D^{22}$: 1.5132 |
| 60 | $C_2H_5$ | $C_3H_7$—n | $CH_2-CH_2-OCH_3$ | $C_2H_5$ | S | 70 | $n_D^{22}$: 1.5043 |
| 61 | $OCH_3$ | $CH_3$ | 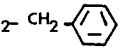 | $C_2H_5$ | S | 77 | $n_D^{23}$: 1.5340 |
| 62 | $NH-C_3H_7$—iso | $C_2H_5$ | $C_2H_5$ | $CH_3$ | S | 73 | $n_D^{22}$: 1.5190 |
| 63 | $C_2H_5$ | $C_2H_5$ | 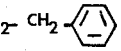 | $C_2H_5$ | S | 82 | $n_D^{23}$: 1.5386 |
| 64 | $C_2H_5$ | $CH_3$ | 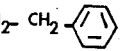 | $C_2H_5$ | S | 73 | $n_D^{22}$: 1.5444 |
| 65 | $SC_3H_7$—n | $C_2H_5$ | $C_2H_5$ | $C_2H_5$ | S | 48 | $n_D^{21}$: 1.5149 |
| 66 | $NH-CH_3$ | $C_2H_5$ | $C_2H_5$ | $C_2H_5$ | S | 53 | $n_D^{21}$: 1.5210 |
| 67 | $NH-CH_2-CH=CH_2$ | $C_2H_5$ | $C_2H_5$ | $C_2H_5$ | S | 60 | $n_D^{21}$: 1.5170 |
| 68 | $NH-C_2H_5$ | $C_2H_5$ | $C_2H_5$ | $C_2H_5$ | S | 51 | $n_D^{22}$: 1.5102 |
| 69 | $OC_3H_7$—iso | $C_3H_7$—iso | $C_2H_5$ | $C_2H_5$ | S | 61 | $n_D^{22}$: 1.4859 |
| 70 | $CH_3$ | $C_3H_7$—iso | $C_2H_5$ | $C_2H_5$ | S | 53 | $n_D^{23}$: 1.5059 |
| 71 |  | $C_2H_5$ | $C_2H_5$ | $C_2H_5$ | S | 49 | $n_D^{23}$: 1.5051 |
| 72 |  | $C_2H_5$ | $C_2H_5$ | $CH\begin{smallmatrix}CH_3\\C_2H_5\end{smallmatrix}$ | S | 72 | $n_D^{24}$: 1.5318 |
| 73 | $C_2H_5$ | $CH_3$ | $C_2H_5$ | $CH\begin{smallmatrix}CH_3\\C_2H_5\end{smallmatrix}$ | S | 45 | $n_D^{24}$: 1.4910 |
| 74 | $C_2H_5$ | $C_2H_5$ | $C_2H_5$ | $CH\begin{smallmatrix}CH_3\\C_2H_5\end{smallmatrix}$ | S | 53 | $n_D^{24}$: 1.4947 |
| 75 | $CH_3$ | $C_2H_5$ | $C_2H_5$ | $CH\begin{smallmatrix}CH_3\\C_2H_5\end{smallmatrix}$ | S | 33 | $n_D^{24}$: 1.4912 |
| 76 | $OCH_3$ | $CH_3$ | $C_2H_5$ | $CH\begin{smallmatrix}CH_3\\C_2H_5\end{smallmatrix}$ | S | 53 | $n_D^{24}$: 1.4840 |
| 77 | $OC_2H_5$ | $C_2H_5$ | $C_2H_5$ | $CH\begin{smallmatrix}CH_3\\C_2H_5\end{smallmatrix}$ | S | 29 | $n_D^{24}$: 1.4692 |
| 78 | $NH-C_3H_7$—iso | $C_2H_5$ | $C_2H_5$ | $CH\begin{smallmatrix}CH_3\\C_2H_5\end{smallmatrix}$ | S | 46 | $n_D^{24}$: 1.4821 |
| 79 | $OC_3H_7$—iso | $C_3H_7$—iso | $C_2H_5$ | $CH\begin{smallmatrix}CH_3\\C_2H_5\end{smallmatrix}$ | S | 48 | $n_D^{24}$: 1.4756 |
| 80 | $OC_4H_9$—n | $C_4H_9$—n | $C_2H_5$ | $CH\begin{smallmatrix}CH_3\\C_2H_5\end{smallmatrix}$ | S | 50 | $n_D^{24}$: 1.4748 |
| 82 | $C_2H_5$ | $CH_3$ | $CH\begin{smallmatrix}CH_3\\C_2H_5\end{smallmatrix}$ | $C_3H_7$—iso | S | 53 | $n_D^{24}$: 1.4880 |
| 81 | $C_2H_5$ | $C_2H_5$ | $CH\begin{smallmatrix}CH_3\\C_2H_5\end{smallmatrix}$ | $C_3H_7$—iso | S | 52 | $n_D^{24}$: 1.4753 |
| 83 | $OCH_3$ | $CH_3$ | $CH\begin{smallmatrix}CH_3\\C_2H_5\end{smallmatrix}$ | $C_3H_7$—iso | S | 56 | $n_D^{24}$: 1.4780 |
| 84 | $NH-C_3H_7$—iso | $C_2H_5$ | $CH\begin{smallmatrix}CH_3\\C_2H_5\end{smallmatrix}$ | $C_3H_7$—iso | S | 51 | $n_D^{24}$: 1.4850 |

Table 2-continued

| Compound No. | $R_1$ | $R_2$ | $R_3$ | $R_4$ | X | Yield (% of theory) | Refractive index |
|---|---|---|---|---|---|---|---|
| 85 | $OC_2H_5$ | $C_2H_5$ | $CH(CH_3)(C_2H_5)$ | $C_3H_7$—iso | S | 57 | $n_D^{24}$: 1.4745 |
| 86 | $C_6H_5$ | $C_2H_5$ | $CH(CH_3)(C_2H_5)$ | $C_3H_7$—iso | S | 62 | $n_D^{24}$: 1.5135 |
| 87 | $C_2H_5$ | $CH_3$ | $CH(CH_3)(C_2H_5)$ | $C_2H_5$ | S | 49 | $n_D^{24}$: 1.4940 |
| 88 | $OCH_3$ | $CH_3$ | $CH(CH_3)(C_2H_5)$ | $C_2H_5$ | S | 41 | $n_D^{24}$: 1.4905 |
| 89 | $OC_2H_5$ | $C_2H_5$ | $C_2H_5$ | 2-Cl-$C_6H_4$ | O | 70 | $n_D^{24}$: 1.5186 |
| 90 | $C_2H_5$ | $C_2H_5$ | $C_2H_5$ | 2-Cl-$C_6H_4$ | S | 70 | $n_D^{24}$: 1.5539 |
| 91 | $CH_3$ | $C_2H_5$ | $C_2H_5$ | 2-Cl-$C_6H_4$ | S | 54 | $n_D^{24}$: 1.5578 |
| 92 | $OC_2H_5$ | $C_2H_5$ | $C_2H_5$ | 3-Cl-$C_6H_4$ | S | 73 | $n_D^{24}$: 1.5435 |
| 93 | $C_2H_5$ | $C_2H_5$ | $C_2H_5$ | 4-Br-$C_6H_4$ | S | 56 | $n_D^{24}$: 1.5606 |
| 94 | $CH_3$ | $C_2H_5$ | $C_2H_5$ | 4-Br-$C_6H_4$ | S | 58 | $n_D^{24}$: 1.5639 |
| 95 | $OCH_3$ | $CH_3$ | $C_2H_5$ | 4-Br-$C_6H_4$ | S | 53 | $n_D^{24}$: 1.5595 |
| 96 | $C_2H_5$ | $C_2H_5$ | $C_2H_5$ | 4-$NO_2$-$C_6H_4$ | S | 21 | $n_D^{24}$: 1.5639 |
| 97 | $CH_3$ | $C_2H_5$ | $C_2H_5$ | 4-$NO_2$-$C_6H_4$ | S | 22 | $n_D^{24}$: 1.5593 |
| 98 | $OCH_3$ | $CH_3$ | $C_2H_5$ | 4-$NO_2$-$C_6H_4$ | S | 20 | $n_D^{24}$: 1.5558 |
| 99 | $C_2H_5$ | $C_2H_5$ | $C_2H_5$ | 2-$CH_3$-4-Cl-$C_6H_3$ | S | 66 | $n_D^{24}$: 1.5500 |
| 100 | $CH_3$ | $C_2H_5$ | $C_2H_5$ | 2-$CH_3$-4-Cl-$C_6H_3$ | S | 60 | $n_D^{24}$: 1.5522 |
| 101 | $OCH_3$ | $CH_3$ | $C_2H_5$ | 2-$CH_3$-4-Cl-$C_6H_3$ | S | 52 | $n_D^{24}$: 1.5490 |
| 102 | $OC_2H_5$ | $C_2H_5$ | $C_2H_5$ | 2,3-$Cl_2$-$C_6H_3$ | O | 74 | $n_D^{24}$: 1.5304 |

Table 2-continued

| Compound No. | $R_1$ | $R_2$ | $R_3$ | $R_4$ | X | Yield (% of theory) | Refractive index |
|---|---|---|---|---|---|---|---|
| 103 | $C_2H_5$ | $C_2H_5$ | $C_2H_5$ | 2,3-dichlorophenyl | S | 60 | $n_D^{24}$: 1.5569 |
| 104 | $CH_3$ | $C_2H_5$ | $C_2H_5$ | 2,3-dichlorophenyl | S | 50 | $n_D^{24}$: 1.5648 |
| 105 | $OC_2H_5$ | $C_2H_5$ | $C_2H_5$ | 2,3-dichlorophenyl | S | 63 | $n_D^{24}$: 1.5304 |
| 106 | $CH_3$ | $C_2H_5$ | $C_2H_5$ | phenyl | S | 32 | $n_D^{24}$: 1.5638 |
| 107 | $OC_2H_5$ | $C_2H_5$ | $C_2H_5$ | phenyl | S | 30 | $n_D^{24}$: 1.5543 |
| 108 | $C_2H_5$ | $C_2H_5$ | $C_2H_5$ | phenyl | S | 25 | $n_D^{24}$: 1.5623 |
| 109 | $OC_2H_5$ | $C_2H_5$ | $C_2H_5$ | 3-methoxyphenyl | S | 31 | $n_D^{24}$ 1.5349 |
| 110 | $CH_3$ | $C_2H_5$ | $C_2H_5$ | 3-methoxyphenyl | S | 33 | $n_D^{24}$: 1.5358 |
| 111 | $C_2H_5$ | $C_2H_5$ | $C_2H_5$ | 3-methoxyphenyl | S | 25 | $n_D^{24}$: 1.5684 |

Other compounds which can be similarly prepared include:

EXAMPLE 3

$LT_{100}$ test for Diptera
Test insects: *Musca domestica*
Solvent: Acetone

| Compound No. | $R_1$ | $R_2$ | $R_3$ | $R_4$ | X |
|---|---|---|---|---|---|
| 112 | $N(CH_2-CH=CH_2)_2$ | $C_2H_5$ | $CH_2CH_2Br$ | 2-isopropoxyphenyl | S |
| 113 | $N(C_2H_5)_2$ | $C_2H_5$ | $CH_2CH_2F$ | $C_2H_5$ | S |
| 114 | $OC_2H_5$ | cyclopentyl | $CH_2COOC_3H_7i$ | 2-isopropylphenyl | S |
| 115 | $OC_2H_5$ | $C_2H_5$ | $CH_2$-phenyl | 4-cyanophenyl | S |
| 116 | $OC_4H_8OC_4H_9$ | $C_4H_8OC_4H_9$ | $C_4H_8OC_4H_9$ | $C_4H_9$ | S |

2 parts by weight of active compound are dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 3

($LT_{100}$ test for Diptera/Musca domestica)

| Active compound | Active compound concentration of the solution, in % | $LT_{100}$ in mins.(') or hours (h) |
|---|---|---|
| (C) | 0.2 | $6^h = 0\%$ |
| (2) | 0.2 | 35' |
|  | 0.02 | 55' |
|  | 0.002 | $6^h = 90\%$ |
| (6) | 0.2 | 70' |
|  | 0.02 | 145' |
| (1) | 0.2 | 35' |
|  | 0.02 | 70' |
| (32) | 0.2 | 35' |
|  | 0.02 | 80' |
|  | 0.002 | $6^h = 40\%$ |
| (34) | 0.2 | 40' |
|  | 0.02 | 75' |
|  | 0.002 | $6^h$ |
| (31) | 0.2 | 50' |
|  | 0.02 | 100' |
|  | 0.002 | $6^h = 70\%$ |
| (5) | 0.2 | 50' |
|  | 0.02 | 70' |
|  | 0.002 | 220' |
| (37) | 0.2 | 35' |
|  | 0.02 | 70' |
|  | 0.002 | $6^h = 80\%$ |
| (36) | 0.2 | 40' |
|  | 0.02 | 100' |
|  | 0.006 | $6^h = 60\%$ |
| (38) | 0.2 | 25' |
|  | 0.02 | 75' |
|  | 0.002 | 210' |
| (40) | 0.2 | 30' |
|  | 0.02 | 70' |
|  | 0.002 | $6^h$ |
|  | 0.0002 | $6^h = 40\%$ |
| (41) | 0.2 | 55' |
|  | 0.02 | 220' |
| (75) | 0.2 | 45' |
|  | 0.02 | 140' |
| (42) | 0.2 | 30' |
|  | 0.02 | 70' |
|  | 0.002 | $6^h$ |
| (73) | 0.2 | 60' |
|  | 0.02 | 160' |
|  | 0.002 | $6^h = 30\%$ |
| (43) | 0.2 | 35' |
|  | 0.02 | 70' |
|  | 0.002 | 240' |
| (82) | 0.2 | 60' |
|  | 0.02 | 110' |
|  | 0.002 | $6^h = 80\%$ |
| (87) | 0.2 | 55' |
|  | 0.02 | 150' |

EXAMPLE 4

$LT_{100}$ test for Diptera
Test insects: *Aedes aegypti*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 4

($LT_{100}$ test for Diptera/Aedes aegypti)

| Active compound | Active compound concentration of the solution, in % | $LT_{100}$ in minutes (') or hours (h) |
|---|---|---|
| (B) | 0.2 | 60' |
|  | 0.02 | 60' |
|  | 0.002 | $3^h = 0\%$ |
| (37) | 0.2 | 60' |
|  | 0.02 | 60' |
|  | 0.002 | 120' |
| (36) | 0.2 | 60' |
|  | 0.02 | 60' |
|  | 0.002 | 180' |
| (38) | 0.2 | 60' |
|  | 0.02 | 60' |
|  | 0.002 | 120' |
| (43) | 0.2 | 60' |
|  | 0.02 | 60' |
|  | 0.002 | 180' |
| (34) | 0.2 | 60' |
|  | 0.02 | 60' |
|  | 0.002 | 180' |
| (5) | 0.2 | 60' |
|  | 0.02 | 60' |
|  | 0.002 | 120' |
| (42) | 0.2 | 60' |
|  | 0.02 | 60' |
|  | 0.002 | 180' |

EXAMPLE 5

$LD_{100}$ test
Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined.

The active compounds, the concentrations of the active compounds, the test insects and the results can be seen from the following table.

Table 5

| Active compound | (LD₁₀₀ test/Sitophilus granarius) Active compound concentration of the solution, in % | Degree of destruction in % |
|---|---|---|
| (C) | 0.2 | 0 |
| (27) | 0.2 | 100 |
| | 0.02 | 100 |
| | 0.002 | 50 |
| (9) | 0.2 | 100 |
| | 0.02 | 100 |
| (2) | 0.2 | 100 |
| | 0.02 | 100 |
| (6) | 0.2 | 100 |
| | 0.02 | 100 |
| (1) | 0.2 | 100 |
| | 0.02 | 100 |
| (44) | 0.2 | 100 |
| | 0.02 | 100 |
| | 0.002 | 100 |
| (45) | 0.2 | 100 |
| | 0.02 | 100 |
| | 0.002 | 40 |
| (30) | 0.2 | 100 |
| | 0.02 | 100 |
| (28) | 0.2 | 100 |
| | 0.02 | 100 |
| (32) | 0.2 | 100 |
| | 0.02 | 100 |
| (34) | 0.2 | 100 |
| | 0.02 | 100 |
| | 0.002 | 80 |
| (31) | 0.2 | 100 |
| | 0.02 | 100 |
| (5) | 0.2 | 100 |
| | 0.02 | 100 |
| | 0.002 | 90 |
| (37) | 0.2 | 100 |
| | 0.02 | 100 |
| | 0.002 | 100 |
| (38) | 0.2 | 100 |
| | 0.02 | 100 |
| | 0.002 | 90 |
| (41) | 0.2 | 100 |
| | 0.02 | 100 |
| (75) | 0.2 | 100 |
| | 0.02 | 100 |
| (42) | 0.2 | 100 |
| | 0.02 | 100 |
| (73) | 0.2 | 100 |
| | 0.02 | 100 |
| (43) | 0.2 | 100 |
| | 0.02 | 100 |
| | 0.002 | 50 |
| (82) | 0.2 | 100 |
| | 0.02 | 100 |
| (87) | 0.2 | 100 |
| | 0.02 | 100 |

EXAMPLE 6

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed.

The active compounds, the concentrations of the active compounds, the evaluation times and the degree of destruction can be seen from the following table:

Table 6

| Active compound | (Drosophila test) Active compound concentration in % | Degree of destruction in % after 1 day |
|---|---|---|
| (C) | 0.1 | 80 |
| | 0.01 | 0 |
| (54) | 0.01 | 100 |
| | 0.001 | 100 |
| (15) | 0.01 | 100 |
| | 0.001 | 100 |
| | 0.0001 | 100 |
| (52) | 0.01 | 100 |
| | 0.001 | 100 |
| (27) | 0.01 | 100 |
| | 0.001 | 100 |
| (4) | 0.01 | 100 |
| | 0.001 | 100 |
| (37) | 0.01 | 100 |
| | 0.001 | 100 |
| | 0.0001 | 100 |
| (2) | 0.01 | 100 |
| | 0.001 | 100 |
| | 0.0001 | 100 |
| (32) | 0.01 | 100 |
| | 0.001 | 100 |
| | 0.0001 | 100 |
| (70) | 0.01 | 100 |
| | 0.001 | 100 |
| (44) | 0.01 | 100 |
| | 0.001 | 100 |
| | 0.0001 | 90 |
| (65) | 0.01 | 100 |
| | 0.001 | 100 |
| (11) | 0.01 | 100 |
| | 0.001 | 100 |
| (31) | 0.01 | 100 |
| | 0.001 | 100 |
| | 0.0001 | 100 |
| (38) | 0.01 | 100 |
| | 0.001 | 100 |
| | 0.0001 | 100 |
| (1) | 0.01 | 100 |
| | 0.001 | 100 |
| | 0.0001 | 100 |
| (45) | 0.01 | 100 |
| | 0.001 | 100 |
| | 0.0001 | 100 |
| (35) | 0.01 | 100 |
| | 0.001 | 98 |
| (36) | 0.01 | 100 |
| | 0.001 | 100 |
| | 0.0001 | 100 |
| (34) | 0.01 | 100 |
| | 0.001 | 100 |
| | 0.0001 | 100 |
| (87) | 0.01 | 100 |
| | 0.001 | 100 |
| (58) | 0.01 | 100 |
| | 0.001 | 100 |
| (51) | 0.01 | 100 |
| | 0.001 | 65 |
| (43) | 0.01 | 100 |
| | 0.001 | 100 |
| | 0.0001 | 100 |
| (40) | 0.01 | 100 |
| | 0.001 | 100 |
| | 0.0001 | 100 |
| (42) | 0.01 | 100 |
| | 0.001 | 100 |
| | 0.0001 | 100 |
| (46) | 0.01 | 100 |
| | 0.001 | 100 |
| | 0.0001 | 100 |
| (85) | 0.01 | 100 |
| | 0.001 | 100 |
| (82) | 0.01 | 100 |
| | 0.001 | 100 |
| (76) | 0.01 | 100 |
| | 0.001 | 99 |
| (73) | 0.01 | 100 |
| | 0.001 | 100 |
| (75) | 0.01 | 100 |
| | 0.001 | 100 |
| (108) | 0.01 | 100 |
| | 0.001 | 99 |
| (5) | 0.01 | 100 |

Table 6-continued

| Active compound | (Drosophila test) Active compound concentration in % | Degree of destruction in % after 1 day |
|---|---|---|
| | 0.001 | 100 |

EXAMPLE 7

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 7

| Active compound | (Plutella test) Active compound concentration in % | Degree of destruction in % after 3 days |
|---|---|---|
| (B) | 0.1 | 100 |
| | 0.01 | 0 |
| (C) | 0.1 | 60 |
| | 0.01 | 0 |
| (37) | 0.1 | 100 |
| | 0.01 | 100 |
| (44) | 0.1 | 100 |
| | 0.01 | 100 |
| (38) | 0.1 | 100 |
| | 0.01 | 100 |
| (1) | 0.1 | 100 |
| | 0.01 | 100 |
| (45) | 0.1 | 100 |
| | 0.01 | 100 |
| | 0.001 | 85 |
| (36) | 0.1 | 100 |
| | 0.01 | 100 |
| (34) | 0.1 | 100 |
| | 0.01 | 100 |
| | 0.001 | 60 |
| (87) | 0.1 | 100 |
| | 0.01 | 100 |
| (50) | 0.1 | 100 |
| | 0.01 | 100 |
| (48) | 0.1 | 100 |
| | 0.01 | 100 |
| (60) | 0.1 | 100 |
| | 0.01 | 100 |
| (8) | 0.1 | 100 |
| | 0.01 | 100 |
| (6) | 0.1 | 100 |
| | 0.01 | 100 |
| (43) | 0.1 | 100 |
| | 0.01 | 100 |
| (40) | 0.1 | 100 |
| | 0.01 | 100 |
| (42) | 0.1 | 100 |
| | 0.01 | 100 |
| (46) | 0.1 | 100 |
| | 0.01 | 100 |
| | 0.001 | 75 |
| (82) | 0.1 | 100 |
| | 0.01 | 100 |
| (73) | 0.1 | 100 |
| | 0.01 | 100 |

Table 7-continued

| Active compound | (Plutella test) Active compound concentration in % | Degree of destruction in % after 3 days |
|---|---|---|
| (96) | 0.1 | 100 |
| | 0.01 | 100 |
| (97) | 0.1 | 100 |
| | 0.01 | 100 |

EXAMPLE 8

Test with parasitic fly larvae/*Lucilia cuprina*
Solvent: 35 parts by weight of ethylene polyglycol monomethyl ether
Emulsifier: 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained about 2 cm$^3$ of horse muscle. 0.5 ml of the preparation of active compound was applied to this horse meat. After 24 hours, the degree of destruction in % was determined. 100% means that all the larvae had been killed and 0% means that no larvae had been killed.

The results obtained can be seen from the table which follows:

Table 8

| Active compound | (Test with parasitic fly larvae/Lucilia cuprina) Active compound concentration in ppm | Degree of destruction in % |
|---|---|---|
| (3) | 100 | 100 |
| | 30 | 100 |
| | 10 | 100 |
| | 3 | 100 |
| (6) | 100 | 100 |
| | 30 | 100 |
| | 10 | 100 |
| | 3 | 100 |
| | 1 | 100 |
| | 0.3 | 100 |
| | 0.1 | <50 |
| (7) | 100 | 100 |
| | 30 | 100 |
| | 10 | 100 |
| | 3 | 100 |
| (11) | 100 | 100 |
| | 30 | 100 |
| | 10 | 100 |
| | 3 | 100 |
| (13) | 100 | 100 |
| | 10 | <50 |
| (19) | 100 | 100 |
| | 10 | <50 |
| (2) | 100 | 100 |
| | 30 | 100 |
| | 10 | 100 |
| | 3 | 100 |
| (1) | 100 | 100 |
| | 30 | 100 |
| | 10 | 100 |
| | 3 | 100 |
| | 1 | 100 |
| | 0.3 | 100 |
| | 0.1 | <50 |
| (15) | 100 | 100 |
| | 30 | 100 |
| | 10 | 100 |
| | 3 | 100 |
| | 1 | 100 |
| (34) | 100 | 100 |
| | 30 | 100 |
| | 10 | 100 |
| | 3 | 100 |
| | 1 | 100 |

Table 8-continued

| (Test with parasitic fly larvae/Lucilia cuprina) | | |
|---|---|---|
| Active compound | Active compound concentration in ppm | Degree of destruction in % |
| | 0.3 | <50 |
| (35) | 100 | 100 |
| | 30 | 100 |
| | 10 | <50 |
| (36) | 100 | 100 |
| | 30 | 100 |
| | 10 | 100 |
| | 3 | 100 |
| | 1 | 100 |
| (37) | 100 | 100 |
| | 30 | 100 |
| | 10 | 100 |
| | 3 | 100 |
| | 1 | 100 |
| (31) | 100 | 100 |
| | 30 | 100 |
| | 10 | 100 |
| | 3 | 100 |
| | 1 | 100 |
| (39) | 100 | 100 |
| | 30 | 100 |
| | 10 | 100 |
| | 3 | 100 |
| (40) | 100 | 100 |
| | 30 | 100 |
| | 10 | 100 |
| | 3 | 100 |
| | 1 | 100 |
| | 0.3 | <50 |
| (43) | 100 | 100 |
| | 30 | 100 |
| | 10 | 100 |
| | 3 | 100 |
| | 1 | 100 |
| (44) | 100 | 100 |
| | 30 | 100 |
| | 10 | 100 |
| | 3 | 100 |
| | 1 | 100 |
| (46) | 100 | 100 |
| | 30 | 100 |
| | 10 | 100 |
| | 3 | 100 |
| | 1 | 100 |
| (38) | 100 | 100 |
| | 30 | 100 |
| | 10 | 100 |
| | 3 | 100 |
| | 1 | 100 |
| (65) | 100 | 100 |
| | 30 | 100 |
| | 10 | 100 |
| | 3 | 100 |
| (66) | 100 | 100 |
| | 30 | 100 |
| | 10 | 100 |
| (67) | 100 | 100 |
| | 30 | 100 |
| | 10 | 100 |
| | 3 | 100 |
| (68) | 100 | 100 |
| | 30 | 100 |
| | 10 | 100 |
| | 3 | 100 |
| (69) | 100 | 100 |
| | 30 | 100 |
| (70) | 100 | 100 |
| | 30 | 100 |
| | 10 | 100 |
| | 3 | 100 |
| (47) | 100 | 100 |
| | 100 | 100 |
| | 30 | 100 |
| (51) | 10 | 100 |
| | 3 | 100 |
| | 1 | <50 |
| | 0.3 | 0 |
| | 100 | 100 |
| (52) | 30 | 100 |
| | 10 | 100 |
| | 3 | 0 |
| | 100 | 100 |
| | 30 | 100 |
| (59) | 10 | 100 |
| | 3 | <50 |
| | 1 | 0 |
| | 100 | 100 |
| | 30 | 100 |
| (60) | 10 | 100 |

Table 8-continued

| (Test with parasitic fly larvae/Lucilia cuprina) | | |
|---|---|---|
| Active compound | Active compound concentration in ppm | Degree of destruction in % |
| | 3 | 100 |
| | 1 | 0 |
| | 100 | 100 |
| (62) | 30 | 100 |
| | 10 | 100 |
| | 3 | 0 |
| | 100 | 100 |
| (63) | 30 | 100 |
| | 10 | 100 |
| | 3 | 0 |

EXAMPLE 9

Critical concentration test
Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test insects. The concentration of the active compound in the preparation was of practically no importance; only the amount of active compound per unit volume of soil, which is given in ppm was decisive. The soil was filled into pots, lettuce was sown in and the pots were kept at a greenhouse temperature of 27°C. After 4 weeks, the lettuce roots were examined for infestation with the insects, and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compound, the amounts applied and the results can be seen from the following table:

Table 9

| (Tenebrio molitor larvae in the soil) | |
|---|---|
| Active compound | Degree of destruction in % at an active compound concentration of 10 ppm |
| (B) | 0 |
| (A) | 0 |
| (40) | 100 |
| (43) | 100 |
| (44) | 100 |
| (73) | 100 |
| (82) | 100 |

EXAMPLE 10

Critical concentration test/soil insects
Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which is heavily infested with the test insects. The concentration of the active compound in the preparation was of practically no importance; only the amount of active compound per unit volume of soil, which is given in ppm, was decisive. The soil was filled into pots, lettuce was sown in and the pots were kept at a greenhouse temperature of 27°C. After 4 weeks, the lettuce roots were examined for infestation with the insects, and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compound, the amounts applied and the results can be seen from the following table:

Table 10

| Active compound | (Phorbia antiqua grubs in the soil) Active compound concentration in ppm | Degree of destruction in % |
|---|---|---|
| (B) | 10 | 0 |
| (A) | 10 | 0 |
| (34) | 5 | 100 |
| (38) | 5 | 98 |
| (43) | 2.5 | 100 |
| (40) | 2.5 | 100 |
| (45) | 5 | 100 |
| (46) | 5 | 100 |
| (51) | 5 | 100 |
| (52) | 5 | 98 |
| (54) | 5 | 90 |
| (59) | 5 | 90 |
| (60) | 5 | 100 |
| (64) | 10 | 95 |
| (73) | 5 | 100 |
| (74) | 5 | 98 |
| (82) | 2.5 | 100 |
| (84) | 5 | 100 |
| (87) | 5 | 100 |
| (90) | 5 | 90 |

It will be appreciated that the instant specification and examples are set forth by way of illustration and not limitation, and that various modifications and changes may be made without departing from the spirit and scope of the present invention.

What is claimed is:

1. A substituted S-carboxymethyl(thiono)-(di)-thiolphosphoric(phosphonic) acid ester or ester-amide of the formula

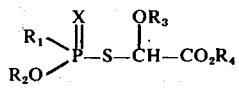

in which
R$_1$ is phenyl or C$_1$–C$_5$ alkyl,
R$_2$ is C$_1$–C$_6$ alkyl, alkoxyalkyl with 1 to 5 carbon atoms in each alkyl moiety or C$_5$–C$_7$ cycloalkyl,
R$_3$ is phenyl; cyclohexyl; C$_1$–C$_7$ alkyl; C$_1$–C$_5$ halogenoalkyl; or carbalkoxymethyl, phenylalkyl or alkoxyalkyl with 1 to 5 carbon atoms in each alkyl moiety,
R$_4$ is C$_1$–C$_5$ alkyl, phenyl or phenyl substituted by at least one of halogen, nitrile, nitro, C$_1$–C$_4$ alkyl and C$_1$–C$_4$ alkoxy, and
X is oxygen or sulfur.

2. A compound according to claim 1, in which R$_1$ is straight-chain or branched C$_1$–C$_4$ alkyl or phenyl, R$_2$ is straight-chain or branched C$_1$–C$_4$ alkyl, C$_5$–C$_6$ cycloalkyl or alkoxyalkyl with 1 to 4 carbon atoms per alkyl moiety, R$_3$ is straight-chain or branched C$_1$–C$_6$ alkyl, halogenoalkyl with 1 to 4 carbon atoms, carbalkoxymethyl with 1 to 4 carbon atoms in the alkyl moiety, alkoxyalkyl with 1 to 4 carbon atoms per alkyl moiety, phenylalkyl with 1 to 4 carbon atoms in the alkyl moiety, phenyl or cyclohexyl, and R$_4$ is straight-chain or branched C$_1$–C$_4$ alkyl, phenyl or phenyl substituted by at least one of nitro, chlorine, bromine, methyl, ethyl, methoxy and ethoxy.

3. The compound according to claim 1 wherein such compound is O-ethyl-S-(1-isopropoxy-1-carbethoxymethyl)-ethanethionothiolphosphonic acid ester of the formula

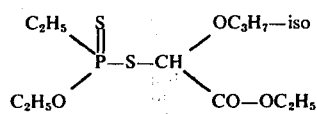

4. The compound according to claim 1 wherein such compound is O-ethyl-S-[1-ethoxy-1-(carbo-2,4-dichlorophenoxy)-methyl]-ethanethionothiolphosphonic acid ester of the formula

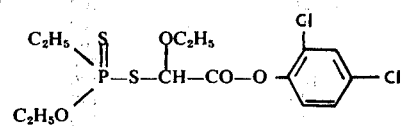

5. The compound according to claim 1 wherein such compound is O-ethyl-S-(1-isopropoxy-1-carbethoxymethyl)-methane thionothiolphosphonic acid ester of the formula

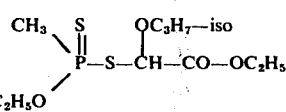

6. The compound according to claim 1 wherein such compound is O-ethyl-S-(1-ethoxy-1-carbethoxymethyl)-methanethionothiolphosphonic acid ester of the formula

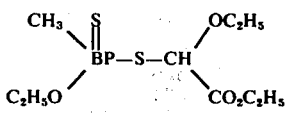

7. The compound according to claim 1 wherein such compound is O-ethyl-S-(1-n-propoxy-1-carbethoxymethyl)-ethanethionothiolphosphonic acid ester of the formula

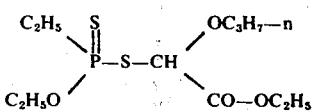

8. An insecticidal composition containing as active ingredient an insecticidally effective amount of a compound according to claim 1 in admixture with a diluent.

9. A method of combating insects which comprises applying to the insects or an insect habitat an insecticidally effective amount of a compound according to claim 1.

10. The method according to claim 9 in which said compound is

O-ethyl-S-(1-isopropoxy-1-carbethoxy-methyl)-ethanethionothiolphosphonic acid ester, O-ethyl-S-[1-ethoxy-1-(carbo-2,4-dichlorophenoxy)-methyl]-ethanethionothiolphosphonic acid ester, O-ethyl-S-(1-isopropoxy-1-carbethoxy-methyl)-methanethionothiolphosphonic acid ester, O-ethyl-S-(1-ethoxy-1-carbethoxy-methyl)-methanethionothiolphosphonic acid ester, or O-ethyl-S-(1-n-propoxy-1-carbethoxy-methyl)-ethanethionothiolphosphonic acid ester.

* * * * *